(12) United States Patent
Karim et al.

(10) Patent No.: US 6,638,891 B2
(45) Date of Patent: Oct. 28, 2003

(54) MOLYBDENUM AND VANADIUM BASED CATALYSTS FOR THE OXIDATION OF ALKANES TO CARBOXYLIC ACIDS AND OLEFINS

(75) Inventors: Khalid Karim, Burnage (GB); Mohammad H. Al-Hazmi, Riyadh (SA); Asad Khan, Riyadh (SA); Syed Irshad Zaheer, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 10/337,657

(22) Filed: Jan. 7, 2003

(65) Prior Publication Data

US 2003/0100794 A1 May 29, 2003

Related U.S. Application Data

(62) Division of application No. 09/561,364, filed on Apr. 28, 2000, now Pat. No. 6,531,631.

(51) Int. Cl.[7] ................................. B01J 23/22
(52) U.S. Cl. .................. 502/302; 502/304; 502/305; 502/306; 502/307; 502/308; 502/309; 502/310; 502/312
(58) Field of Search ................. 502/302, 304, 502/305, 306, 307, 308, 309, 310, 312

(56) References Cited

U.S. PATENT DOCUMENTS

| | | |
|---|---|---|
| 4,148,759 A | 4/1979 | Hilfman |
| 4,246,427 A | 1/1981 | Andoh |
| 4,250,346 A | 2/1981 | Young et al. |
| 4,289,654 A | 9/1981 | Bertolini |
| 4,339,355 A | 7/1982 | Decker et al. |
| 4,358,608 A | 11/1982 | Shaw et al. |
| 4,524,236 A | 6/1985 | McCain |
| 4,568,790 A | 2/1986 | McCain |
| 4,596,787 A | 6/1986 | Manyik et al. |
| 4,654,801 A | 3/1987 | Stewart et al. |
| 4,849,003 A | 7/1989 | Kawamura |
| 5,153,162 A | 10/1992 | Kurimoto et al. |
| 5,162,578 A | 11/1992 | McCain, Jr. et al. |
| 5,807,531 A | 9/1998 | Hibst |
| 5,907,056 A | 5/1999 | Karim et al. |
| 5,959,143 A | 9/1999 | Sugi |
| 6,028,221 A | 2/2000 | Karim et al. |
| 6,030,920 A | 2/2000 | Karim et al. |
| 6,034,270 A | 3/2000 | Borchert |
| 6,060,421 A | 5/2000 | Karim et al. |
| 6,084,126 A | 7/2000 | Hibst |
| 6,087,297 A | 7/2000 | Karim et al. |
| 6,184,173 B1 | 2/2001 | Hibst |
| 6,194,610 B1 | 2/2001 | Borchert |
| 6,274,765 B1 | 8/2001 | Borchert |
| 6,310,241 B1 | 10/2001 | Karim et al. |
| 6,399,816 B1 | 6/2002 | Borchert |

FOREIGN PATENT DOCUMENTS

| | | |
|---|---|---|
| DE | 3300044 | 7/1983 |
| DE | 19815281 | 10/1999 |
| EP | 0 293 859 A1 | 7/1988 |
| EP | 293859 | 12/1988 |
| EP | 427508 | 5/1991 |
| EP | 685259 | 12/1995 |
| EP | 711745 | 5/1996 |
| EP | 774297 | 5/1997 |
| JP | 4321642 | 11/1992 |
| JP | 5317713 | 12/1993 |
| JP | 5329371 | 12/1993 |
| JP | 11343261 | 12/1999 |

*Primary Examiner*—Paul J. Killos
(74) *Attorney, Agent, or Firm*—Kramer Levin Naftalis & Frankel LLP

(57) ABSTRACT

A mixed metal oxide catalytic system for producing olefins and carboxylic acids from lower alkanes comprising a catalyst composition having the formula $$Mo_a V_b Al_c X_d Y_e O_z$$

wherein:
  X is at least one element selected from the group consisting of W and Mn;
  Y is at least one element selected from the group consisting of Pd, Sb, Ca, P, Ga, Ge, Si, Mg, Nb, and K;
  a is 1;
  b is 0.01 to 0.9;
  c is >0 to 0.2;
  d is >0 to 0.5;
  e is >0 to 0.5; and
  z is an integer representing the number of oxygen atoms required to satisfy the valency of Mo, V, Al, X, and Y.

8 Claims, No Drawings

MOLYBDENUM AND VANADIUM BASED CATALYSTS FOR THE OXIDATION OF ALKANES TO CARBOXYLIC ACIDS AND OLEFINS

This application is a Divisional of application Ser. No. 09/561,364 filed on Apr. 28, 2000 now U.S. Pat. No. 6,531,631.

BACKGROUND OF THE INVENTION

1. Field of the Invention

The present invention relates to new catalysts for the production of alkenes by selective, partial oxidation of the corresponding alkane and to methods of producing such catalysts and methods of using the same. More particularly, this invention relates to tungsten or manganese-based catalysts for the selective, partial oxidation of alkanes to the corresponding value added product, such as ethylene and acetic acid, with high selectivity, depending on the type of the metal oxide catalyst used in the process.

2. Description of the Related Art

Several publications are referenced in this application. These references describe the state of the art to which this invention pertains, and are incorporated herein by reference.

Many catalysts have been proposed for the activation of light alkane hydrocarbons in oxidation and oxidative dehydrogenation reactions. Some of these catalytic systems make use of one or more catalysts in order to maximize the yield of value added product, e.g., acetic acid via oxidative dehydrogenation of ethane. E. M. Thorsteinson, T. P. Wilson and F. G. Young, *Journal of Catalysis*, 2:116–132 (1970) were the first to report the use of a molybdenum and vanadium-based mixed metal oxide catalyst for the production of ethane to ethylene. Several other publications have described the use of different catalytic systems for such reactions, including U.S. Pat. Nos. 5,162,578, 4,524,236, 4,568,790, 4,250,346, 5,153,162, 5,907,566, 4,849,003, 4,596,787, 4,339,355, and 4,148,759; European patent application nos. 0294845, 0480594, 0407091, 0518548, and 0627401; WO 9913980; WO 9805620; and U.S. application Ser. Nos. 09/107,115, 09/219,702, 08/997,913, 09/107,046, and 09/085,347.

Due to the great industrial importance of oxygenated hydrocarbons and dehydrogenated products, even a slight improvement in the redox behavior of the metal oxide catalyst, responsible for the activation and product selectivity, can impact tremendously on the catalyst's performance and strength. Ultimately, such improvements can have a remarkable commercial and economic impact on the process. Therefore, it would be desirable to produce a metal oxide catalyst having improved or modified redox properties which can achieve the goals of high product selectivity or activity.

SUMMARY OF THE INVENTION

The present invention provides a method for the selective oxidation of lower alkanes, e.g., ethane, with molecular oxygen to yield the corresponding carboxylic acid and/or olefin, e.g., acetic acid and ethylene, at relatively high selectivity and productivity. The process is carried out at temperatures of 150° C. to 450° C. and pressures of 1–50 bar. The method is achieved using catalyst compositions containing mixed metal oxides.

The catalyst compositions of the present invention include compositions of the formula:

$$Mo_a V_b Al_c X_d Y_e O_z$$

wherein:
X is at least one element selected from the group consisting of W and Mn;
Y is at least one element selected from the group consisting of Pd, Sb, Ca, P, Ga, Ge, Si, Mg, Nb, and K;
a is 1;
b is 0.01 to 0.9;
c is >0 to 0.2;
d is >0 to 0.5;
e is >0 to 0.5; and
z is an integer representing the number of oxygen atoms required to satisfy the valency of Mo, V, Al, X, and Y. The catalysts are preferably produced using the methods disclosed herein.

DETAILED DESCRIPTION OF PREFERRED EMBODIMENTS

One aspect of the invention relates to a catalyst for the production of olefins and carboxylic acids from lower alkanes via a selective, partial oxidation. In a preferred embodiment, the method of the present invention provides a means for the selective partial oxidation of ethane to yield acetic acid and ethylene.

The catalyst compositions of the present invention comprise compositions of the formula:

$$Mo_a V_b Al_c X_d Y_e O_z$$

wherein:
X is at least one element selected from the group consisting of W and Mn;
Y is at least one element selected from the group consisting of Pd, Sb, Ca, P, Ga, Ge, Si, Mg, Nb, and K;
a is 1;
b is 0.01 to 0.9;
c is >0 to 0.2;
d is >0 to 0.5;
e is >0 to 0.5; and
z is an integer representing the number of oxygen atoms required to satisfy the valence of Mo, V, Al, X, and Y. The catalysts of the present invention can be used with or without a support. The choice of the individual elements contained in the catalyst composition as well as the specific procedures followed in preparing the catalyst can have a significant impact on the performance of a catalyst.

Preferably, the catalyst is prepared from a solution of soluble compounds (salts, complexes, or other compounds) of each of the metals. The solution is preferably an aqueous system having a pH of 1 to 10, and more preferably a pH of 1 to 7, and it is maintained at a temperature of about 30° C. to about 100° C. After the elements are combined in solution, water is removed by filtration, and the catalyst is dried, e.g., in an oven at a temperature from 100° C. to 130° C. The dried catalyst is calcined by heating to a temperature of about 250° C. to about 600° C., preferably about 250° C. to about 450° C., in air or oxygen for about one hour to about 16 hours to yield the desired catalyst composition.

Suitable supports for the catalyst include alumina, silica, titania, zirconia, zeolites, silicon carbide, molybdenum carbide, molecular sieves and other microporous/nonporous materials, and mixtures thereof. Support materials can be pretreated with acids, such as HCl, $HNO_3$, $H_2SO_4$, per acids or heteropoly acids, and alkali bases. When used with a support, the composition usually comprises from about 5% to 50% by weight catalyst, with the remainder being the support material.

Preferably, molybdenum is introduced into the solution in the form of an ammonium salt, such as ammonium paramolybdate, or as an organic acid salt of molybdenum, such as an acetate, oxalate, mandelate, or glycolate. Some other partially water soluble molybdenum compounds which may be used to prepare the catalyst compositions of the present invention include molybdenum oxides, molybdic acid, and chlorides of molybdenum. Preferably, vanadium, aluminum, gallium, silicon, germanium, antimony, phosphorous, niobium, potassium, magnesium, palladium, tungsten, and manganese are introduced into the catalyst slurry as salts or acids, including but not limited to oxides, hydrate oxides, acetates, chlorides, nitrate acetates, oxalates, oxides, and tartrates.

The present method may be used to oxidize lower alkanes, e.g., $C_2$–$C_8$ alkanes, preferably ethane, propane, and n-butane, as well as alpha-beta unsaturated aliphatic aldehydes. In a preferred embodiment, the starting material is ethane. The starting material(s) may be in the fluid or gas phase. If the starting material(s) is in the fluid phase, the catalyst may convert the reactant(s) to one or more fluid products. The starting material(s) may also be supplied in a gas stream, which contains at least five volume percent of ethane or a mixture of ethane and ethylene. The gas stream can also contain minor amounts of $C_3$–$C_4$ alkanes and alkenes, with the proviso that the gas stream contain less than five volume percent of each. The gas stream can also contain major amounts, i.e., more than five volume percent, of nitrogen, carbon dioxide, and steam.

The reaction mixture used in carrying out the process is generally a gaseous mixture of 0.1 to 99 mol % ethane, 0.1 to 99 mol % molecular oxygen, either as pure oxygen or air, and zero to 50 mol % steam. In a preferred embodiment, the feed mixture contains 0.1–50% by volume molecular oxygen. Further, water may be added as a reaction diluent and as a heat moderator for the reaction. Water added as a co-feed in this way can also act as a desorption accelerator of the reaction product in the vapor phase oxidation reaction or to mask the sites responsible for total oxidation resulting in an increased yield of acetic acid. The amount of oxygen present may be equal to or less than a stoichiometric amount of oxygen in relation to the amount of hydrocarbons in the feed.

The gaseous mixture is generally introduced into the reaction zone at a temperature of about 150° C. to about 450° C., and preferably 200° C. to 300° C. The reaction zone generally has a pressure of 1 to 50 bar, and preferably 1 to 30 bar, a contact time between the reaction mixture and the catalyst of about 0.01 seconds to 100 seconds, preferably 0.1 seconds to 50 seconds, and most preferably 0.1–10 seconds, and a space hourly velocity of about 50 to about 50,000 $h^{-1}$, preferably 100 to 10,000 $h^{-1}$, and most preferably 200 to 3,000 $h^{-1}$. The process is generally carried out in a single stage in a fixed bed or fluidized bed reactor with all the oxygen and reactants being supplied as a single feed. Non-reacted starting materials can be recycled. However, multiple stage additions of oxygen to the reactor with intermediate hydrocarbon feed can also be used. This may improve the productivity of the process and avoid a potentially hazardous condition due to explosion limits of the mixture of hydrocarbons and oxidants.

The catalyst of the invention is not limited to use in the oxydehydrogenation of ethane to acetic acid. The catalyst of the present invention may also be used (1) to oxidize alpha-beta unsaturated aliphatic aldehydes in the vapor phase with molecular oxygen to produce the corresponding alpha-beta unsaturated carboxylic acids, (2) to oxidize $C_3$ alkanes or alkenes to the corresponding acids, and (3) to ammoxidize alkanes and/or alkenes. In a preferred embodiment, the method is used to selectively oxidize ethane, with little or no carbon monoxide as a side product. In one embodiment, the maximum amount of carbon monoxide produced is about 2% based on percent selectivity. Further, the method yields product at a selectivity preferably of at least 80%, more preferably at least 82%, and even more preferably at least 90%, and a conversion rate preferably of at least 7%.

The following examples are intended to be illustrative of this invention. They are, of course, not to be taken to in any way limit the scope of this invention. Numerous changes and modifications can be made with respect to the invention without departing from the spirit or scope of the present invention.

EXAMPLES

Example 1

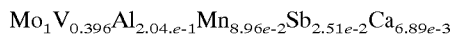

Ammonium metavanadate (Aldrich Chemicals, Assay= 99.0%), 5.7 grams, was added to distilled water and heated to 90° C. with stirring. A yellow colored solution with a pH between 4 and 7 was obtained (solution A). Antimony trioxide, 0.45 grams, and 11 grams of oxalic acid were added with water to solution A with continuous stirring, and the required amounts of calcium, aluminum, and manganese salts were slowly added to the mixture. Thereafter, ammonium paramolybdate tetrahydrate (Aldrich Chemicals A.C.S-12054-85-2), 21.7 grams, was added to the solution. This mixture was dried and the resulting solid was put in an oven at 100–120° C. The dried material was cooled to room temperature and calcined at 300 to 600° C.

The calcined catalyst was formulated into uniform particles of 40–60 mesh size and loaded into a stainless steel fixed bed tubular autoclave reactor. The catalyst was tested with a gas containing a mixture of ethane, oxygen, and nitrogen in a ratio of each starting material of 50:10:40 at 260° C., at a pressure of 200 psi and a total flow of 24 cc/min. The reaction yielded product at 21.46% ethane conversion with a selectivity of 30% acetic acid, 62% ethylene, and 8% $CO_x$ products.

Example 2

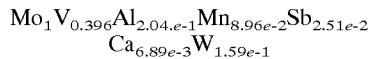

Ammonium metavanadate (Aldrich Chemicals, Assay= 99.0%), 5.7 grams, was added to distilled water and heated to 90° C. with stirring. A yellow colored solution with a pH between 4 and 7 was obtained (solution A). Antimony trioxide, 0.45 grams, and 11 grams of oxalic acid were added with water to solution A with continuous stirring, and the required amount of calcium, aluminum, manganese, and tungsten solutions were slowly added to the mixture. Thereafter, ammonium paramolybdate tetrahydrate (Aldrich Chemicals A.C.S-12054-85-2), 21.7 grams, was added to the solution. This mixture was dried and the resulting solid was put in an oven at 120° C. The dried material was cooled to room temperature and calcined at 300 to 600° C.

The calcined catalyst was formulated into uniform particles of 40–60 mesh size and loaded into a stainless steel fixed bed tubular autoclave reactor. The catalyst was tested with a gas feed composition of ethane, oxygen, and nitrogen in a ratio of each starting material of 50:10:40 at 260° C., at a pressure of 200 psi and a total flow of 24 cc/min. The reaction exhibited an 11% rate of ethane conversion with a selectivity of 19% acetic acid, 70% ethylene, and 11% $CO_x$ products.

Example 3

$$Mo_1V_{0.396}Al_{2.25e-1}Mn_{8.96e-2}Sb_{2.51e-2}Ca_{6.89e-3}Pd_{2.88e-4}$$

Ammonium metavanadate (Aldrich Chemicals, Assay=99.0%), 5.7 grams, was added to distilled water and heated to 90° C. with stirring. A yellow colored solution with pH between 4 and 7 was obtained (solution A). Antimony trioxide, 0.45 grams, and 12 grams of oxalic acid were added with water to solution A with continuous stirring, and the required amount of calcium, aluminum, palladium, and manganese solutions were slowly added to the mixture. Thereafter, ammonium paramolybdate tetrahydrate (Aldrich Chemicals A.C.S-12054-85-2), 21.7 grams, was added to the solution. This mixture was then dried and the resulting solid was put in an oven at 120° C. The dried material was cooled to room temperature and calcined at 300 to 600° C.

The calcined catalyst was formulated into uniform particles of 40–60 mesh size and loaded in a stainless steel fixed bed tubular autoclave reactor. The catalyst was tested with a gas feed composition of ethane, oxygen, and nitrogen in the ratio of each starting material of 50:10:40 at 260° C., at a pressure of 200 psi and a total flow of 24 cc/min. The reaction showed 8% ethane conversion with a selectivity of 71% acetic acid, 22% ethylene, and 7% $CO_x$ products.

Example 4

$$MO_1V_{0.396}Al_{2.04.e-1}W_{1.59e-1}Pd_{2.60e-4}$$

Ammonium metavanadate (Aldrich Chemicals, Assay=99.0%), 5.7 grams, was added to distilled water and heated to 90° C. with stirring. A yellow colored solution with pH between 4 and 7 was obtained (solution A). Oxalic acid, 11 grams, was added with water to solution A with continuous stirring, and the required amount of calcium, aluminum, and manganese salts were slowly added to the mixture. Thereafter, ammonium paramolybdate tetrahydrate (Aldrich Chemicals A.C.S-12054-85-2), 21.7 grams, was added to the solution. This mixture was then dried and the resulting solid was put in an oven at 120° C. The dried material was cooled to room temperature and calcined at 300 to 600° C.

The calcined catalyst was formulated into uniform particles of 40–60 mesh size and loaded in a stainless steel fixed bed tubular autoclave reactor. The catalyst was tested with a gas feed composition of ethane, oxygen, and nitrogen in a ratio of each starting material of 50:10:40 at 260° C., at a pressure of 200 psi and a total flow of 24 cc/min. The reaction showed a 9% of ethane conversion with a selectivity of 75% acetic acid, 3% ethylene, and 23% $CO_x$ products.

A high selectivity of the partial oxidation products such as ethylene or acetic acid for the catalyst disclosed in the invention showed that the redox properties of the resultant mixed metal oxide catalysts are modified. This could be due to generation of different types of active phases formed by the right combination of these metal oxides resulting in a significant impact on the selectivity or activity. In addition, the catalysts of the present invention exhibit enhanced stability/life. Catalysts are not deactivated until 4000 hours or more on stream. Lower ΔT of the reaction (lower than 4° C.) demonstrates that the chances of the generation of hot spots responsible for rapid decay or sintering of the catalyst are very minimal. Accordingly, the catalysts have a reasonable lifetime.

We claim:

1. A catalyst composition for selective partial oxidation of lower alkanes to produce olefins and carboxylic acids, said composition having the formula:

$$Mo_aV_bAl_cX_dY_eO_z$$

wherein:
X is at least one element selected from the group consisting of W and Mn;
Y is at least one element selected from the group consisting of Pd, Sb, Ca, P, Ga, Ge, Si, Mg, Nb, and K;
a is 1;
b is 0.01 to 0.9;
c is >0 to 0.2;
d is >0 to 0.5;
e is >0 to 0.5; and
z is an integer representing the number of oxygen atoms required to satisfy the valency of Mo, V, Al, X, and Y.

2. The catalyst composition of claim 1, further comprising a support.

3. The catalyst composition of claim 2, wherein said support is selected from the group consisting of alumina, silica, titania, zirconia, zeolites, silicon carbide, molecular sieves, microporous or nonporous materials, and mixtures thereof.

4. The catalyst composition of claim 2, wherein said support is pretreated with acidic or alkali materials.

5. The catalyst composition of claim 4, wherein said support is pretreated with an acid selected from the group consisting of HCl, $H_2SO_4$, $HNO_3$, and heteropoly acids.

6. The catalyst composition of claim 4, wherein said support is pretreated with a base selected from the group consisting of KOH and NaOH.

7. The catalyst composition of claim 2, wherein said composition comprises 5–50% by weight catalyst and 50–95% by weight support.

8. A method of making the catalyst composition of claim 1, comprising forming a mixture of soluble compounds of Mo, V, Al, X and Y in an aqueous solution at a pH from about 1 to about 10, drying the mixture to yield dried solid material, and calcining the dried solid material at a temperature from about 250° C. to about 450° C. for a time of about one hour to about 16 hours.

\* \* \* \* \*